(12) United States Patent
Sorenson et al.

(10) Patent No.: US 8,738,297 B2
(45) Date of Patent: *May 27, 2014

(54) METHOD FOR MOLECULAR GENEALOGICAL RESEARCH

(75) Inventors: James L. Sorenson, Salt Lake City, UT (US); Scott R. Woodward, Alpine, UT (US); Joel Myres, Provo, UT (US); Natalie Myres, legal representative, Provo, UT (US)

(73) Assignee: Ancestry.com DNA, LLC, Provo, UT (US)

( * ) Notice: Subject to any disclaimer, the term of this patent is extended or adjusted under 35 U.S.C. 154(b) by 468 days.

This patent is subject to a terminal disclaimer.

(21) Appl. No.: 13/066,680

(22) Filed: Apr. 20, 2011

(65) Prior Publication Data

US 2013/0149707 A1 Jun. 13, 2013

Related U.S. Application Data

(63) Continuation of application No. 10/113,901, filed on Mar. 29, 2002, now Pat. No. 7,957,907.

(60) Provisional application No. 60/280,226, filed on Mar. 30, 2001.

(51) Int. Cl.
| | | |
|---|---|---|
| *G01N 33/48* | (2006.01) | |
| *G06F 19/00* | (2011.01) | |
| *G01N 31/00* | (2006.01) | |
| *G06G 7/48* | (2006.01) | |

(52) U.S. Cl.
USPC .................... 702/19; 702/20; 702/22; 703/11

(58) Field of Classification Search
None
See application file for complete search history.

(56) References Cited

U.S. PATENT DOCUMENTS

| | | | |
|---|---|---|---|
| 4,201,386 A | 5/1980 | Seale et al. | |
| 5,115,504 A | 5/1992 | Belove et al. | |
| 5,246,374 A | 9/1993 | Boodram | |
| 5,413,908 A | 5/1995 | Jeffreys | |
| 5,467,471 A | 11/1995 | Bader | |
| 5,978,811 A | 11/1999 | Smiley | |
| 6,049,803 A | 4/2000 | Szalwinski | |
| 6,105,147 A | 8/2000 | Molloy | |
| 6,277,567 B1 | 8/2001 | Graziosi | |
| 6,528,260 B1 | 3/2003 | Blumenfeld et al. | |
| 6,570,567 B1 | 5/2003 | Eaton | |
| 2003/0113727 A1 | 6/2003 | Girn et al. | |
| 2003/0204418 A1 | 10/2003 | Ledley | |
| 2004/0122705 A1 | 6/2004 | Sabol et al. | |
| 2004/0243531 A1 | 12/2004 | Dean | |
| 2006/0020398 A1 | 1/2006 | Vernon et al. | |
| 2006/0136143 A1 | 6/2006 | Avinash | |
| 2006/0161535 A1 | 7/2006 | Holbrook | |

OTHER PUBLICATIONS

"Genealogy" definition, Merriam-Webster online dictionary, 2004, on the world wide web at http://www.m-w.com/cgi-bin/dictionary?book=Dictionary&va=genealogy, 1 page.
Butler, John M., Commonly Used Short Tandem Repeat Markers, Forensic DNA Typing, Chapter 5, 2001, pp. 53-54, Academic Press.
Corach et al., "Mass disasters: Rapid molecular screening of human remains by means of short tandem repeats typing" Electrophoresis (1995) vol. 16; pp. 1617-1623.
International Search Report for International Application No. PCT/US07/20884 dated Mar. 10, 2008.
PCT International Preliminary Report on Patentability, PCT/US2007/020884, dated Apr. 16, 2009.
Stedman's Medical Dictionary 27$^{th}$ Edition, 2000, p. 703.
Website printout, Family Tree DNA, http://www.familytreedna.com/main.html, Feb. 8, 2001, 2 pages.
Website printout, Oxford Ancestors, Feb. 12, 2001, 4 pages.
Wilson et al. "Genealogical Inference from Microsatellite Date" Genetics (1998) 150:499-510.

*Primary Examiner* — Eric S Dejong
(74) *Attorney, Agent, or Firm* — TraskBritt, P.C.

(57) ABSTRACT

A genealogical research and record keeping system and method for identifying commonalities in haplotypes and other genetic characteristics of a biological sample of two or more individual members. Chromosomal fragments identical by descent identify family ties between siblings, parents and children and ancestors and progeny across many generations. It is particularly useful in corroborating and improving the accuracy of genealogical data and identifying previously unknown genetic relationships.

15 Claims, 6 Drawing Sheets

Regions of Differential Variation in DNA

| Spacer | Regulatory | Structural |
|---|---|---|
| Almost no selection pressure | Under moderate to strong selection | Under strong selection pressure |
| May have multiple nt changes per 1000 bp's | Possibly 1 nt change in 1000 bp's | Very few variations from person to person |
| INDIVIDUALS & FAMILIES | TRIBES OR CLANS | SPECIES |

Fig. 1

SEQUENCE LISTING

<160> NUMBER OF SEQ ID NOS: 18

<210> SEQ ID NO 1
<211> LENGTH: 19
<212> TYPE: DNA
<213> ORGANISM: Unknown
<220> FEATURE:
<223> OTHER INFORMATION: forward primer

<400> SEQUENCE: 1
cactacccca gggtcatca					19

<210> SEQ ID NO 2
<211> LENGTH: 17
<212> TYPE: DNA
<213> ORGANISM: Unknown
<220> FEATURE:
<223> OTHER INFORMATION: reverse primer

<400> SEQUENCE: 2
gcttcagcct cagcaca					17

<210> SEQ ID NO 3
<211> LENGTH: 17
<212> TYPE: DNA
<213> ORGANISM: Unknown
<220> FEATURE:
<223> OTHER INFORMATION: forward primer

<400> SEQUENCE: 3
agctcacttt tggcctc					17

<210> SEQ ID NO 4
<211> LENGTH: 20
<212> TYPE: DNA
<213> ORGANISM: Unknown
<220> FEATURE:
<223> OTHER INFORMATION: reverse primer

<400> SEQUENCE: 4
tggatcttgg atgttcattc					20

<210> SEQ ID NO 5
<211> LENGTH: 20
<212> TYPE: DNA
<213> ORGANISM: Unknown
<220> FEATURE:
<223> OTHER INFORMATION: forward primer

<400> SEQUENCE: 5
aattgcagcc tgtgagagac					20

<210> SEQ ID NO 6
<211> LENGTH: 20
<212> TYPE: DNA
<213> ORGANISM: Unknown
<220> FEATURE:
<223> OTHER INFORMATION: reverse primer

<400> SEQUENCE: 6
gcctccataa ttgcatgaac					20

<210> SEQ ID NO 7
<211> LENGTH: 16
<212> TYPE: DNA

```
<213> ORGANISM: Unknown
<220> FEATURE:
<223> OTHER INFORMATION: forward primer

<400> SEQUENCE: 7
agaaaccatg cccttg                                                       16

<210> SEQ ID NO 8
<211> LENGTH: 19
<212> TYPE: DNA
<213> ORGANISM: Unknown
<220> FEATURE:
<223> OTHER INFORMATION: reverse primer

<400> SEQUENCE: 8
tgcagtcacc tgtgtagaa                                                    19

<210> SEQ ID NO 9
<211> LENGTH: 20
<212> TYPE: DNA
<213> ORGANISM: Unknown
<220> FEATURE:
<223> OTHER INFORMATION: forward primer

<400> SEQUENCE: 9
tgagttttat tggccaaagc                                                   20

<210> SEQ ID NO 10
<211> LENGTH: 20
<212> TYPE: DNA
<213> ORGANISM: Unknown
<220> FEATURE:
<223> OTHER INFORMATION: reverse primer

<400> SEQUENCE: 10
tctttccatg gatgctgtct                                                   20

<210> SEQ ID NO 11
<211> LENGTH: 20
<212> TYPE: DNA
<213> ORGANISM: Unknown
<220> FEATURE:
<223> OTHER INFORMATION: forward primer

<400> SEQUENCE: 11
gggagtgggg taaaaaaaaa                                                   20

<210> SEQ ID NO 12
<211> LENGTH: 20
<212> TYPE: DNA
<213> ORGANISM: Unknown
<220> FEATURE:
<223> OTHER INFORMATION: reverse primer

<400> SEQUENCE: 12
cctctaaccc ccagaaatgt                                                   20

<210> SEQ ID NO 13
<211> LENGTH: 20
<212> TYPE: DNA
<213> ORGANISM: Unknown
<220> FEATURE:
<223> OTHER INFORMATION: forward primer

<400> SEQUENCE: 13
ttctgatgta atcgacttgc                                                   20
```

```
<210> SEQ ID NO 14
<211> LENGTH: 20
<212> TYPE: DNA
<213> ORGANISM: Unknown
<220> FEATURE:
<223> OTHER INFORMATION: reverse primer

<400> SEQUENCE: 14
ccacccaaac ctaacagata                                           20

<210> SEQ ID NO 15
<211> LENGTH: 22
<212> TYPE: DNA
<213> ORGANISM: Unknown
<220> FEATURE:
<223> OTHER INFORMATION: reverse primer

<400> SEQUENCE: 15
agacagtcaa gaataactgc cc                                        22

<210> SEQ ID NO 16
<211> LENGTH: 20
<212> TYPE: DNA
<213> ORGANISM: Unknown
<220> FEATURE:
<223> OTHER INFORMATION: reverse primer

<400> SEQUENCE: 16
ctgtggctca aaagctgaat                                           20

<210> SEQ ID NO 17
<211> LENGTH: 23
<212> TYPE: DNA
<213> ORGANISM: Unknown
<220> FEATURE:
<223> OTHER INFORMATION: forward primer

<400> SEQUENCE: 17
cagattaact ttctgccaga gag                                       23

<210> SEQ ID NO 18
<211> LENGTH: 20
<212> TYPE: DNA
<213> ORGANISM: Unknown
<220> FEATURE:
<223> OTHER INFORMATION: reverse primer

<400> SEQUENCE: 18
gagtgcccta gatggaaggt                                           20
```

METHOD FOR MOLECULAR GENEALOGICAL RESEARCH

CROSS-REFERENCE TO RELATED APPLICATIONS

This application is a continuation of co-pending U.S. patent application Ser. No. 10/113,901, filed Mar. 29, 2002, now U.S. Pat. No. 7,957,907. U.S. patent application Ser. No. 10/113,901 claims priority under the provisions of 35 U.S.C. §119(e) from Provisional Patent Application Ser. No. 60/280,226, filed Mar. 30, 2001. The disclosure of each of the foregoing is hereby incorporated herein by this reference in its entirety.

TECHNICAL FIELD

This invention relates generally to genealogical research and record keeping, and is specifically directed to identifying commonalities in genetic characteristics correlated with specific genetic markers. The invention provides a system and method particularly useful in corroborating and improving the accuracy of genealogical records and identifying previously unknown genealogical relationships.

BACKGROUND

Genealogical record keeping has traditionally involved isolated efforts to assemble and maintain stores of information about progenitors for progeny. Different cultures have created unique methods for maintaining genealogical records. Some tribes in western Africa, for example, have designated individuals who are reputed to recount by memory the names of scores of generations of ancestry and considerable additional detailed information about many individual ancestors. Most western civilizations have normally maintained written records to store such names and information, including records of births, christenings, marriages, deaths, military, civic and other governmental involvement. Much of this information is accessible on microfiche and on any of a variety of electronic media, including the Internet.

U.S. patents with application to genealogical record keeping include: U.S. Pat. No. 6,049,803 to Szalwinski "Documenting System for Entities, Attributes and Schema of a Relational Database"; U.S. Pat. No. 5,978,811 to Smiley "Information Repository System and Method for Modeling Data"; U.S. Pat. No. 5,467,471 to Bader "Maintaining Databases by means of Hierarchical Genealogical Table"; U.S. Pat. No. 5,246,374 to Boodram "Expandable Family Tree and Modular Kit for Building the Same"; U.S. Pat. No. 5,115,504 to Belove, et al. "Information Management System"; and U.S. Pat. No. 4,201,386 to Seale, et al. "Genealogy Apparatus."

Unfortunately, the history of some people and communities has been lost or destroyed through time. In such instances, written documents are uninformative or simply do not exist. For example, descendants of slaves are often unable to locate any records of their ancestors. Illegitimacy or adoption may obstruct information or prevent access to records of biological ancestors. Similarly, immigration records may not accurately reflect the country of origin or complete surname of an individual. All of these circumstances can present significant obstacles for individuals trying to trace their "roots." Additionally, written information relies, by its nature, on the correctness of the source. Inaccuracies in such records are rife due to limited memory, human error and purposeful efforts to conceal inconvenient or embarrassing facts.

Molecular genealogy merges the science of genetics with the study of genealogy and provides an alternative method of identifying genealogical information. By utilizing the biological genetic record that each individual retains of his/her past coded in the DNA of that individual, it is possible to reveal important clues as to his/her origin and relationship to any other person or population.

Molecular genealogy links individuals together in "family trees" based on the unique identification of genetic markers. A polymorphic genetic marker represents a specific location on a chromosome (locus) where the basic genetic units exist. A difference of a single nucleotide at a particular location on a chromosome is called a Single Nucleotide Polymorphism ("SNP"), or point mutation, and other polymorphisms are determined by the number of short tandem repeats ("STR") of simple sequence DNA. Variant copies at any chromosomal location are termed "alleles." Different combinations of polymorphisms on a particular chromosome can be arranged as haplotypes. The more closely related two individuals are, the more alleles they will share in common. Any two individuals may share alleles at one or a few locations. However, examination of several dozen or hundreds of chromosomal locations will uncover differences even among closely related persons. The compilation of multiple genetic markers is referred to as a genotype and serves as a unique genetic identifier for any given individual. To reconstruct molecular genealogies, it is necessary to utilize known biological relationships and correlate this information with the transmission of genetic markers through time.

Information encoded in the DNA of an individual and/or population can be used to determine the relatedness of individuals, families, tribal groups, and populations. Pedigrees based on genetic markers can reveal relationships not detectable in genealogies based only on names, written records, or oral traditions. The fact that DNA is inherited equally from both biological parents means that DNA can be used not only to create unique identifiers but also to identify members of the same family, the same clan or tribal group, or the same population.

Prior art genetic record keeping systems and methods, fueled significantly by the human genome project, identify genetic characteristics of individual members of human and other species. Some records are directed to genetic characteristics in common between and among two or more individual members of a given biological sample, irrespective of familial relation. Examples of such genetic characteristics include genes determinative of human eye, hair and skin color, height and other physical characteristics. Interspecies analyses and records have been pursued as well, such as the study of commonalities in the genetic makeup of various primates. Similar genetic characteristics may be identified among intrafamilial relations as a portion of a broader lineal genetic inheritance, such as a proclivity toward cancers, heart disease, obesity and other conditions in some family lines. An example of such intrafamilial genetic characteristics is a genetic marker for the cystic fibrosis gene discovered by Scott R. Woodward, Ph.D. et al., then of the University of Utah.

The study of any of a variety of genetic characteristics and their presence among a defined familial group has heretofore focused on medical applications within relatively few generations. Similarly, the nexus of the genealogical and genotypical disciplines finds expression only in a very limited sense in such fields as forensic science and paternity determinations, and then only for a relatively limited number of generations.

Some potential genealogical applications of genetic science are limited in their usefulness, such as the notion that all sons inherit their entire Y-chromosome from their fathers and all children inherit identical mitochondria from their mothers. For example, Y-chromosome genetic markers were analyzed in an attempt to determine whether Thomas Jefferson fathered any illegitimate children with Sally Hemings. Jefferson did not have any known direct male descendants. Therefore, a genetic sample from a known, living male relative of Jefferson's uncle was compared with genetic samples from known living male relatives of Hemings' sons. Scholars debate the conclusiveness of the test but acknowledge a likelihood that Jefferson fathered at least one son with Hemings. However, because Y-chromosome genetic markers were studied, geneticists were unable to determine whether another male relative of Jefferson fathered the children or whether any of Hemings' daughters were related to Jefferson. Similarly, geneticists could not confirm their theories by examining genetic samples from known descendants of Jefferson's daughters.

Similarly, men of Jewish descent can determine whether they are of Cohanim lineage by examination of Y-chromosome genetic markers. Such sex-chromosome investigations are limited because they involve a limited number of genetic markers and are restricted to a particular lineage and a particular sex. As females do not have a Y-chromosome and males do not pass on their mitochondrial DNA, determining whether members of the opposite sex are related can be a complicated, multi-step process.

No known method exists of combining genetic science and genealogical information to enable identification of biological ancestral relations across multiple earlier generations to a degree that is more accurate than that afforded by mere memory or written records. Thus, a need exists for a combination of genotypical and genealogical disciplines to identify chromosomal fragments that are identical by descent to elucidate family ties between siblings, parents and children, and ancestors and progeny across many generations.

A further need exists for a confluence of genetic science and genealogical resources to corroborate and improve the accuracy of genealogical data pertaining to other than strictly paternal or strictly maternal lines of ancestry.

An additional need yet exists to correlate genetic information with genealogical information to identify previously unknown biological relationships.

DISCLOSURE

An embodiment of the invention includes a computer-implemented system for analyzing relatedness including an expandable database for storing a plurality of hierarchical trees, a first user interface for creating a plurality of data fields within at least one tree of the hierarchical trees and a second user interface for adding genetic data to at least one data field. The computer readable storage medium further includes analytical programming for relating and alterably categorizing each data field. Computational means or executable programming describe a genetic pattern for a first tree and correlating means correlates the genetic pattern of the first tree with a genetic pattern for at least a second tree. The computer readable storage medium further includes computational means or executable programming for predicting an antecedent genetic pattern in the first tree.

In an embodiment of the invention, the database includes a plurality of genetic markers for a plurality of members of a population, genealogical records for each member of the population and analytical programming that can cross-reference the genetic markers and genealogical records. The population may be selected from the group consisting of primate, human, canine, equine, caprine, feline, fowl, bovine, ovine and suid. In one embodiment, the genealogical records comprise at least three successively lineal ancestral familial generations and may include populational origin data of the member. In a preferred embodiment, each member of the plurality of members of a population is assigned a unique genetic identifier, having both genetic and genealogical components, such that the genetic markers and genealogical records are stored in association with the unique genetic identifier. In one embodiment, the genetic markers are autosomal and are in linkage disequilibrium.

In another embodiment, a molecular genealogy database comprises genetic markers for each member of a population stored in association with a unique genetic identifier for each member and genealogical records of each member stored in association with the unique genetic identifier for each member. The database may further comprise analytical programming for cross-referencing and comparing the genetic markers and the genealogical records. The genealogical records may comprise at least three successively lineal ancestral familial generations and may include populational origin data. In another embodiment, the genealogical records may comprise pedigree records. The genetic markers may be autosomal and in linkage disequilibrium.

An embodiment of the invention includes a method of identifying genealogical relationships wherein a database is provided having a genetic data set and a genealogical data set relating to a plurality of members of a species. Analytical means are provided that can associate and analyze the genetic data and genealogical data and thereby infer a previously unknown genealogical relationship. The genetic data may be parsable into haplotypical form.

Another embodiment of the invention includes a method of determining the level of biological relatedness by identifying a plurality of members of a species and identifying at least one compound or complex genetic marker for the plurality of members. While the disclosed method is applicable to any species, the species is human in a preferred embodiment. Genealogical data are identified for the plurality of members and a plurality of groups is created. Each member is categorized into at least one group based on the degree of similarity of the at least one genetic marker such that each defined group has a representative genetic marker. The genealogical data are then compared within each defined group and levels of biological relatedness of each categorized member is inferred.

A further embodiment of the invention includes a method of correcting a genealogical family tree by identifying genetic data for a plurality of individuals and identifying a genealogical family tree having a plurality of placeholders. Genetic data are identified and compared for each placeholder. Each placeholder is positioned in a unique location within the family tree based on that placeholder's genetic data. Genetic discrepancies are noted among the plurality of placeholders and any placeholders having genetic data outside of a genetic range are designated as anomalous. The genetic data of the plurality of individuals are compared with the genetic data for each placeholder and at least one individual is identified having genetic data within the genetic range. Of the members having data within the genetic range, at least one individual is identified as being a potential placeholder. Finally, the anomalous placeholder is resolved. For example, the anomalous placeholder can be resolved by removing the anomalous placeholder from the family tree or by substituting a potential placeholder for the anomalous placeholder.

Another embodiment of the invention includes a method of determining populational group origin by providing a database of a plurality of family trees, each family tree having a plurality of placeholders. The database is supplemented with genetic data for at least one placeholder, thereby creating a genetic genealogy for each family tree. The database is also supplemented with population origin data for at least one placeholder, thereby associating the placeholder's family tree with at least one population origin. A genetic sample is obtained and compared with the genetic data in the database and population origin of the genetic sample is inferred.

A further embodiment of the invention includes a method of determining the level of biological relatedness by identifying a plurality of family trees, members of the plurality of family trees and genetic markers representative of the members. At least one unique genetic marker is identified for each family tree. A genetic sample is obtained and compared with the at least one unique genetic marker. The level of biological relatedness of the genetic sample within at least one family tree is inferred based on the degree of correlation of the genetic sample to the unique genetic marker.

The applications of this invention are not limited to humans. The invention may also be used in similar ways to determine or confirm the pedigree of an animal subject such as, but not limited to, a primate, canine, equine, caprine, feline, fowl, bovine, ovine, or suid.

BRIEF DESCRIPTION OF THE DRAWINGS

FIG. 1 illustrates regions of differential variation in DNA.

DETAILED DESCRIPTION OF THE INVENTION

A fundamental principle of genetic transmission, that all persons receive genetic material from their biological parents, allows one to determine the origin of genes based on a common ancestry and known modes of inheritance. Because this process is repeated every generation, all individuals carry within their DNA a record of who they are and how they are related to all of the other people on the earth. As individuals trace their biological relationships into the past, lineages will begin to "coalesce" into common ancestors.

In order to determine the degree of relatedness between individuals, it is necessary to identify those genetic markers that are identical due to shared ancestry. Different regions of DNA have the ability to identify individuals and link them to immediate family groups, extended family or clan affiliations, and larger populations. For example, FIG. 1 illustrates how specific regions of DNA have properties that can identify an individual's identity (DNA sequences associated with spacer regions), extended family or tribe (possible regulatory regions) and species (structural gene regions). The "structural" region of DNA is under strong selection pressure. As such, very few variations are found among individual members of the same species. By way of contrast, the "spacer" region of DNA is under almost no selection pressure. Therefore, an individual, or a family, can be identified by a unique "spacer" sequence. The "regulatory" region of DNA is under moderate to strong selection pressure; less selection pressure than the "structural" region but more than the "spacer" region.

Figure 2:
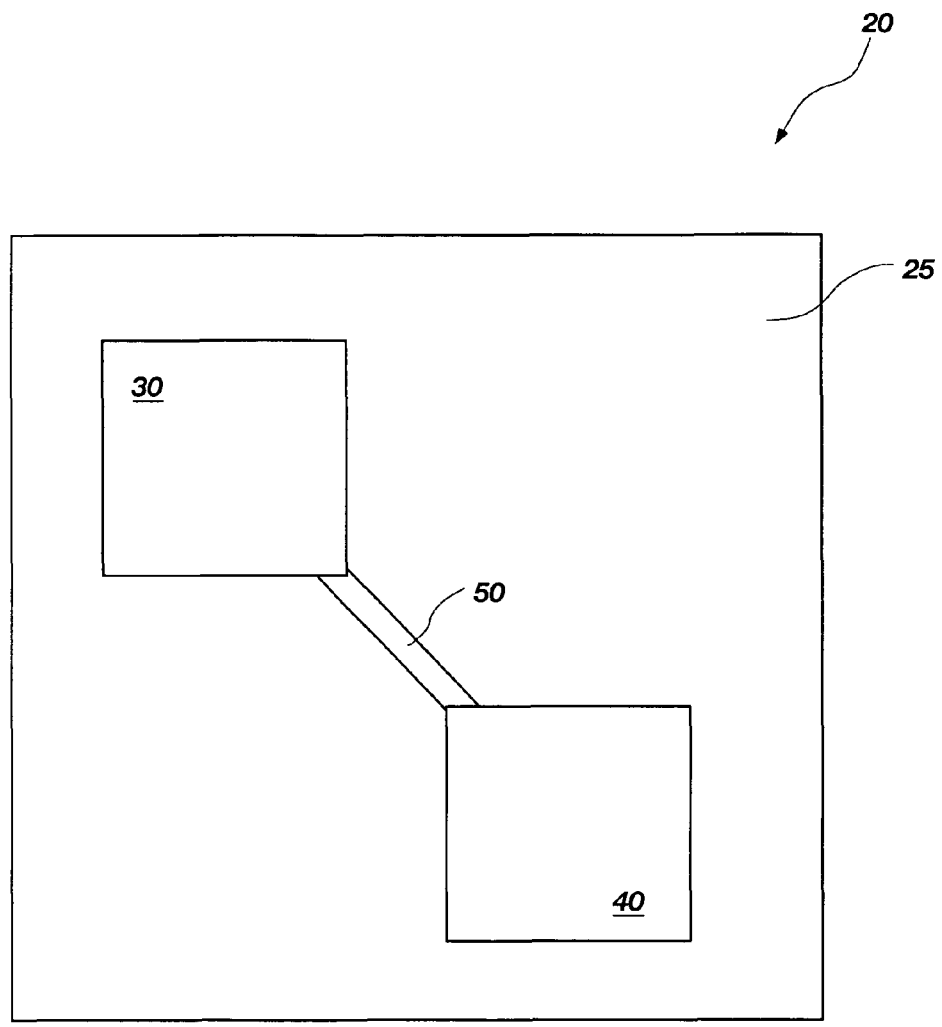
FIG. 2 illustrates a system of molecular genealogical research and record keeping including a database having a data set of genealogical data, a data set of genetic data and analytical programming that can analyze and correlate the genealogical data and genetic data.

FIG. 2 illustrates a system of genealogical research and record keeping designated generally 20, including a database 25 which may be stored, for example, in a computer (not shown). The database 25 can store data sets including genetic data 30 for a plurality of members and corresponding genealogical records or data 40 extending at least three, and often in excess of 10, successively lineal ancestral familial generations. Preferably, the genetic data 30 includes at least one genetic marker, or chromosomal fragment, that is substantially identical by descent. If more than one genetic marker is included in the genetic data, it is preferable that at least one genetic marker is autosomal. More preferably, the majority of genetic markers are autosomal. The genealogical records, when known, preferably include the given name and surname of each ancestor as well as each ancestor's date and place of birth, thus providing a geographic tie to the genetic data. Genealogical records may also include oral family history information, marriage records or other vital records, military records, wills, land deeds, etc. By examining each ancestor's place of birth, an individual can determine his or her populational origin or ethnicity. The genealogical records may also include any additional information that might be of genealogical or genetic interest, for example, medical history, physical characteristics or personal accomplishments of each ancestor.

The database 25 may be created by obtaining a genetic sample and genealogical information from a plurality of individuals. Analytical programming 50 may associate dates of birth and geographical locations with each genetic sample. A plurality of tests may be performed on the genetic sample to identify an allelic state of the individual at a plurality of loci. The genetic information obtained through analysis of the genetic sample is entered into the database and algorithms are applied to identify the most likely haplotype of the individual. Each individual may have between 50-60 haplotypes based on the analysis of sets of genetic markers. An exemplary algorithm is the Haplotyper developed by Brigham Young University.

Figure 3:
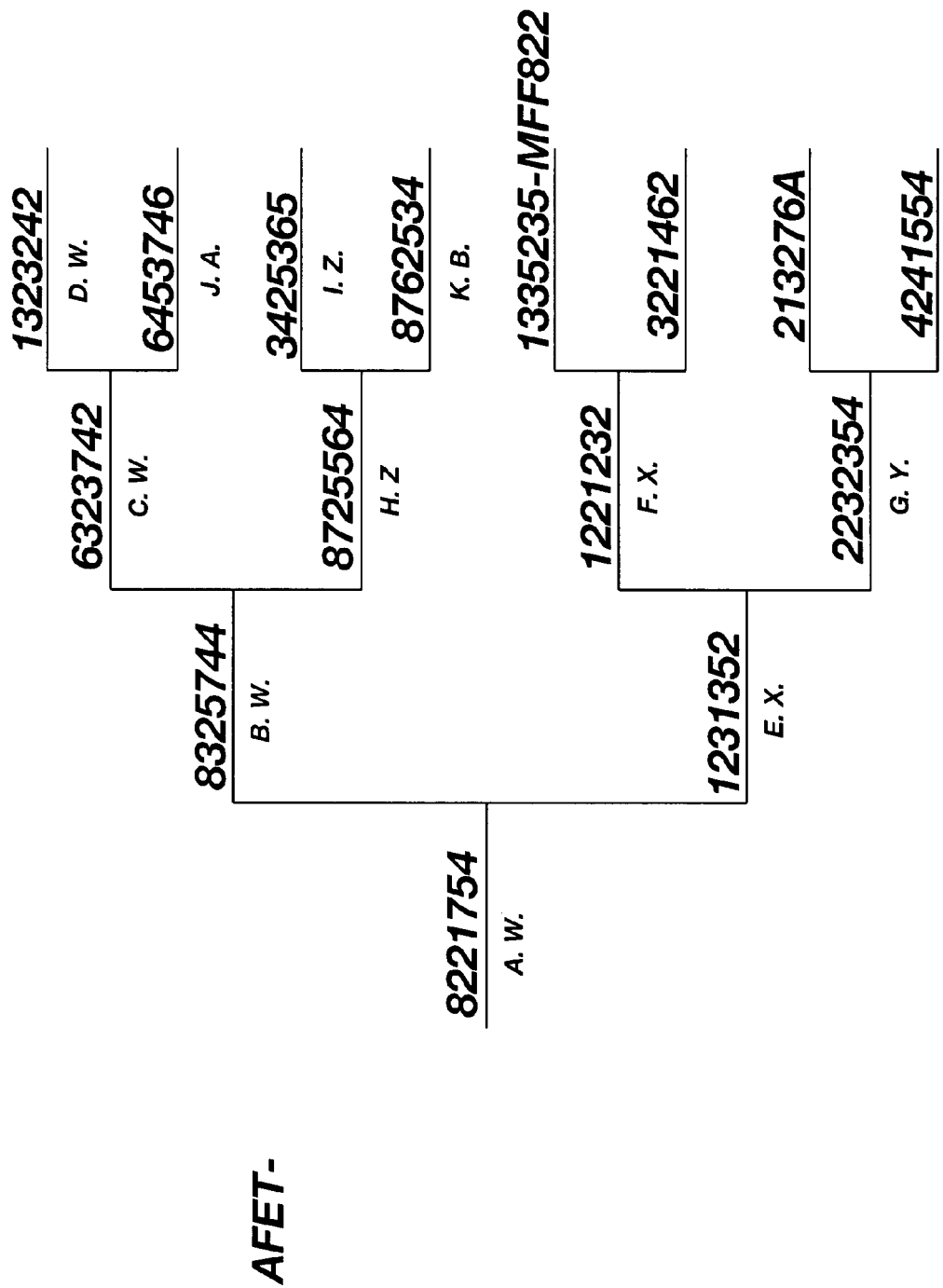
FIG. 3 depicts how unique genetic identifiers could be used in a traditional genealogical chart.
Figure 4:
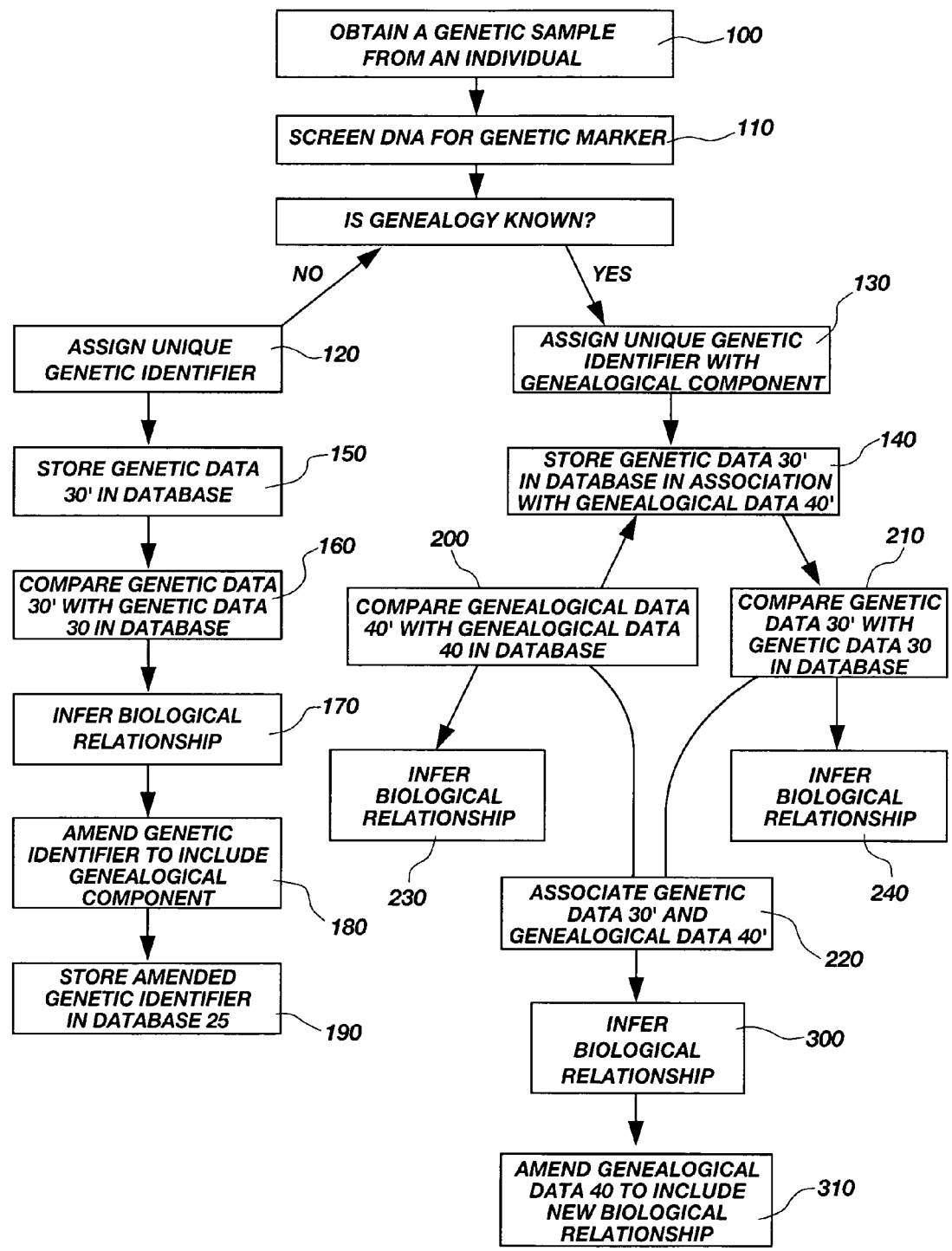
FIG. 4 is a flow chart of a preferred method of the invention.

Analytical programming 50 cross-references and associates the genetic data 30 and the genealogical records 40. For example, genealogical records 40 can be stored in a hierarchical format similar to a "family tree" wherein each individual, or placeholder, within the family tree is assigned a unique genetic identifier (described herein) (FIG. 3). This unique genetic identifier can also be stored in association with each individual's genetic data 30' (FIG. 4). A unique identifier can also be assigned to each hierarchical tree.

The hierarchical tree is then analyzed to identify individuals having a shared common ancestor. The genetic data of these identified individuals is then analyzed to identify shared haplotypes. Based on the analysis of the genetic data, the haplotype of the common ancestor may be discerned based on the at least two lines of descent. Thus, the present invention allows the reconstruction of haplotypes for individuals despite lack of a genetic sample.

The database 25 may be a part of a computer-readable storage medium or a computer-implemented system for analyzing relatedness that also includes at least one user interface. A first user interface can be used for creating a plurality of data fields. Preferably, the data fields will be located within a hierarchal family tree within the database 25. As an example, the data fields could include genealogical data, including but not limited to medical history information, date of birth, place of birth or other information about each placeholder on a family tree. A second user interface can be used for adding genetic data to the data fields. An example of genetic data includes genetic markers and the haplotype of the individual. Analytical programming relates and alterably categorizes each data field. Computational means or executable programming identify and describe a genetic pattern for a given data set, for example, a family tree. A genetic pattern might include a genetic marker, or chromosomal fragment, that is identical by descent. Correlating means correlate the genetic pattern for the first family tree with at least a second family tree. Further, computational means or executable programming predict an antecedent genetic pattern in the first family tree, for example, based on a statistical probability of relatedness.

The computer readable storage medium may further comprise computational means or executable programming for annotating a genetic range within a statistical confidence interval for each hierarchical tree. The computational means or executable programming can compare the genetic range of each hierarchical tree with a genetic range of at least one other tree. Further, each hierarchical tree can be stored in the database in association with a unique identifier that reflects the genetic data of members of each tree.

FIG. 4 illustrates a flow chart of a preferred embodiment of the invention. In step 100, a genetic sample is obtained from an individual. Genetic information can be gathered by obtaining a small blood, saliva or hair sample from an individual. DNA is extracted from the sample in the laboratory and specific regions of DNA are amplified using the polymerase chain reaction ("PCR"). In step 110, the PCR products are analyzed for specific genetic markers.

Several methods exist for identifying those genes or markers that are identical due to shared ancestry. Commonly employed genetic systems used to test relatedness are autosomal genes or markers contained on the autosomes (non-sex chromosomes), the Y-chromosome (Y-cs), and mitochondrial DNA (mtDNA). While chromosomes exist in pairs in the nucleus of every cell, mtDNA is more numerous and is located outside the nucleus in the mitochondria. Chromosomes are subject to recombination or shuffling every generation and are not necessarily inherited intact from generation to generation. This characteristic property of genetics introduces the diversity found among peoples and is one of the mechanisms responsible for the unique genetic identity that defines an individual. Y-cs and mtDNA are novel in that they experience limited or no recombination. Y-cs DNA is inherited from father to son and mtDNA is inherited by all children from their biological mother but only passed on through daughters. Each of these systems can be differentially used to answer various questions of genetic interest.

In a preferred embodiment, at least one of the genetic markers is autosomal, thereby increasing the probability in which genealogical relationships may be inferred between two individuals of the opposite sex. Typically, at least 250 genetic markers will be examined in each genetic sample. The genetic markers may be grouped in sets of 3-5 genetic markers in linkage disequilibrium. Linkage disequilibrium is a condition where two or more genetic markers are found together in a population at a greater frequency than that predicted simply by the product of their individual gene frequencies. Thus, the presence of a gene at a particular location on a chromosome creates a bias at another location. Analysis of sets of genetic markers in linkage disequilibrium allows the determination of unambiguous haplotypes from the genotypic information at a physical location on a chromosome. By identifying markers that are in linkage disequilibrium, there is a significant increase, as compared with unlinked markers, in determining regions of a chromosome that are inherited from one parent or another.

Those of skill in the art will appreciate that selection of the particular genetic markers examined for each genetic sample is a dynamic process and may expand or contract based on the specific population being analyzed. Thus, the particular genetic markers examined are not as important as discerning a hereditary pattern among the genetic markers. There are thousands of known simple repeat genetic markers and millions of characterized single nucleotide polymorphisms ("SNP") that may be analyzed in accordance with the present invention. By way of example, Table 1 depicts genetic markers within three haplogroups on chromosome 2 and corresponding primer sequences as identified by the Marshfield Clinic. Other exemplary genetic markers and short tandem repeat ("STR") loci that may be analyzed for chromosomes 1, 2 and 3 are arranged in potential linkage disequilibrium groups and shown in Table 2, Table 3 and Table 4, respectively.

Potential genetic markers may be selected based on their physical location on a chromosome, known polymorphisms and level of polymorphic information content ("PIC"). Preferably, the genetic marker will have a high PIC value and a physical location such that multiple genetic markers are expected to be in linkage disequilibrium. In one embodiment, two to three sets of genetic markers (each set representing at least three genetic markers) per chromosome are targeted and analyzed on each of the 22 autosomal chromosomes.

Genetic markers may also be analyzed on the Y-chromosome and mtDNA. In one embodiment, twenty-three markers on the Y-cs, representing a haplotype, and 150 SNPs are analyzed in each genetic sample. Further, in one embodiment, 750 nucleotides of the mtDNA D-loop are sequenced. The sex-linked genetic markers are helpful in segregating a group of individuals into large populations and may be combined with the autosomal genetic markers to further define genetic relationships.

As stated, the specific genetic markers examined in each genetic sample may vary through the data collection process. Initially, known haplogroups on autosomal chromosomes may be analyzed to determine behavior. For example, known haplogroups may be examined against genetic samples from individuals of known genetic relationship to confirm that the genetic markers follow standard Mendelian inheritance patterns. Then, the haplogroups may be run against a large data set (i.e., 25,000 to 100,000 samples) wherein the genetic relationship of the members of the data set are not known. The behavior of the haplogroup within the large data set may provide insight regarding the genetic relationship of members as well as verify the usefulness of the selected haplogroup.

If the individual does not have any known biological ancestors, the process moves to step 120 where he or she is assigned a unique genetic identifier based solely on genetic data 30'. The specific genetic markers for an individual creates genetic data 30' for that individual. Compilation of multiple genetic markers for an individual creates a unique genotype that can be used to assign a unique genetic identifier. In step 150, the individual's genetic data 30' is stored in the database 25 in association with the unique genetic identifier.

In step 160, the individual's genetic data 30' is compared with the genetic data 30 in the database 25 and a biological relationship is inferred in step 170 based on the degree of similarity of the data. For example, the genetic data 30 can be categorized into groups such that all members of a group share similar genetic markers. Thus, each defined group has a representative genetic marker. The individual can be assigned to a group based on whether his or her genetic data 30' is statistically similar to the representative genetic marker. Levels of biological relatedness of the members of a group can be inferred based on further similarities and variations of each member's genetic data. Inference of biological relationships and levels of biological relatedness can be further enhanced by cross-referencing each member's genetic data with the corresponding genealogical data. Identification of biological relationships and level of biological relatedness may allow an individual to identify previously unknown biological relations, populational origin and medical history. Genetic markers may be in haplotype form. Further, the size of each defined group can be limited according to the genealogical or genetic data.

The statistical probability that two people are related can be determined by examination of the similarity of their genetic markers as compared with a larger sample. Preferably, the representative genetic marker is within a predetermined confidence interval. Similarly, the representative genetic marker of each defined group and the genealogical data of each group can be statistically correlated. This analysis permits the level of biological relatedness of each defined group to be statistically correlated and determined.

Once a biological relationship has been inferred, the individual's genetic identifier can be amended to include a genealogical component in step 180. The individual's amended genetic data 30' and previously unknown genealogical data 40' can be stored in the database 25 in association with the individual's unique genetic identifier in step 190.

Figure 5:
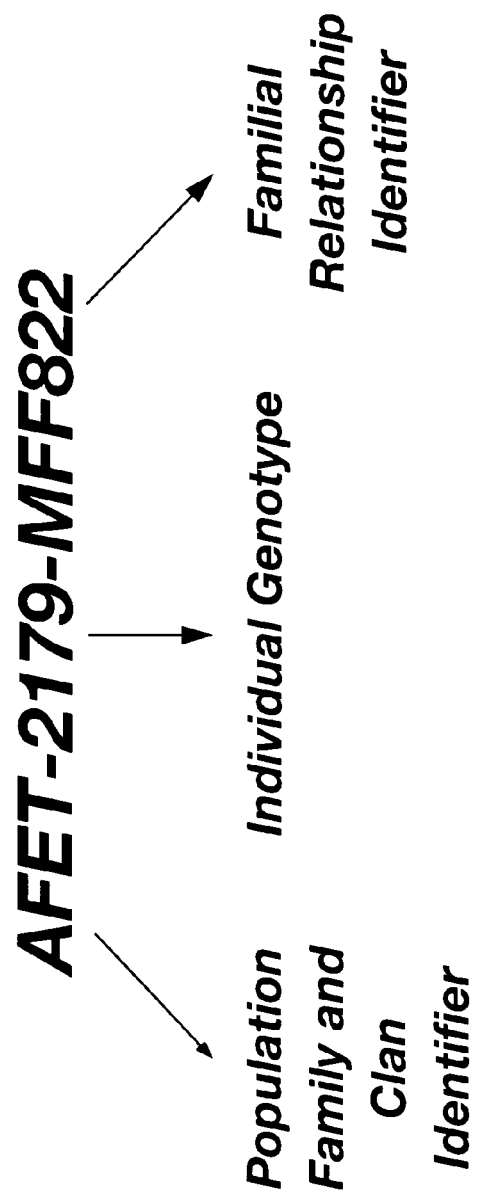
FIG. 5 is an example of a unique genetic identifier of the present invention.

If, instead, genealogical data are known for the individual, the process moves to step 130 where a unique genetic identifier is assigned that reflects the individual's genealogical data 40' and genetic data 30'. In a preferred embodiment, the unique genetic identifier of step 130 includes three segments (FIG. 5). A first segment reflects a population and lineage identifier. For example, in FIG. 5, this segment is designated by "AFET" and all individuals of the same population, family or clan share this segment. Each family tree can be identified by this segment of the unique genetic identifier (FIG. 3). A second segment is the familial relationship identifier. In FIG. 5, this segment is designated MFF822. In this nonlimiting example, the individual represented by FIG. 5 would have an ancestor (his/her mother's (M) father (F), father (F)) that had been assigned the number "822." By associating an individual with the number "822," a degree of relatedness may be gleaned. Finally, a third segment reflects the individual genotype as shown by "2179" in FIG. 5. The individual genotype identifier can also be used within a family tree. As shown in FIG. 3, "A.W." has been assigned the genetic identifier "8221754." The genetic identifier is the true, actual "derived" haplotype of the individual with components that relate the individual to others in the database.

Figure 6:
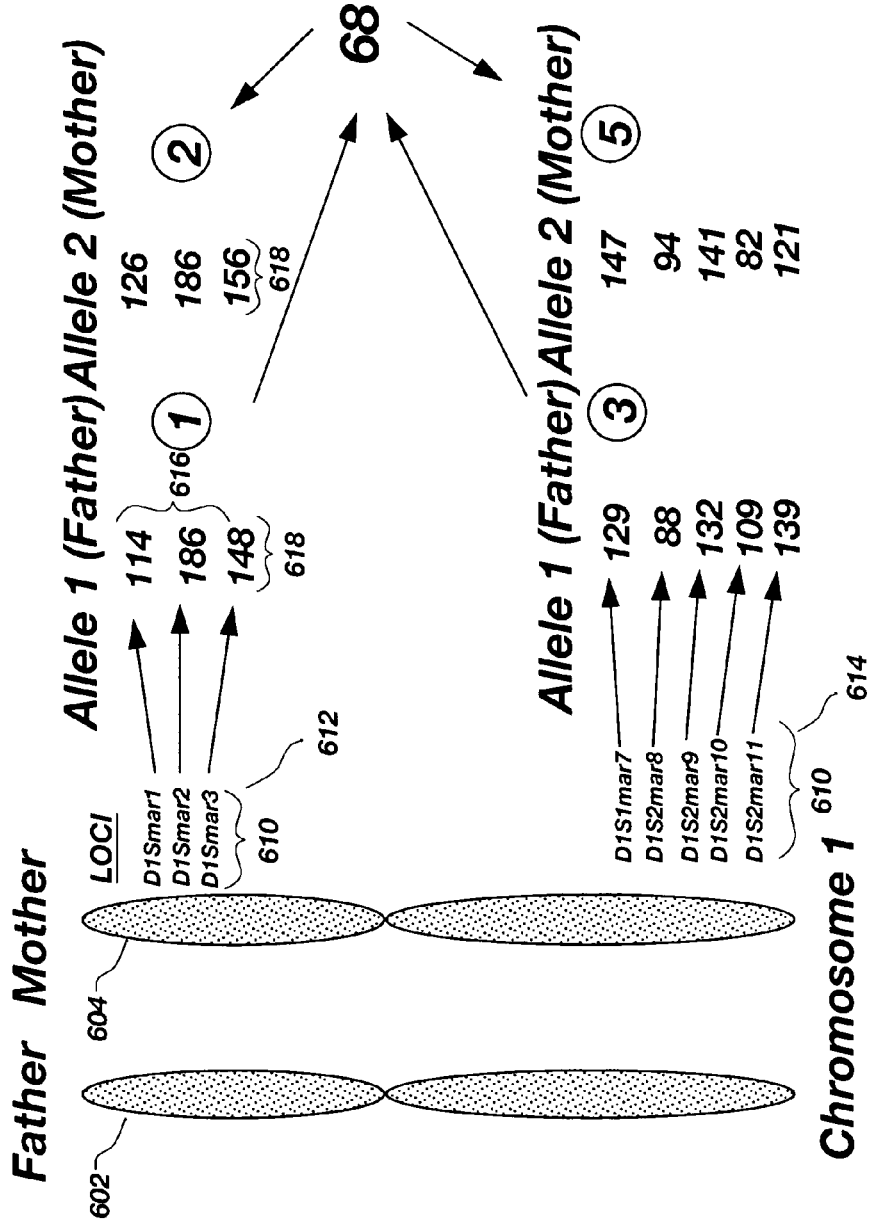
FIG. 6 is an example of chromosome reconstruction.

FIG. 6 illustrates one embodiment of how a specific genetic identifier is constructed. In one embodiment, the genetic identifier comprises a plurality of numbers wherein each number represents a specific genetic component. FIG. 6 depicts an exemplary chromosome reconstruction wherein an individual possesses a pair of chromosomes, one from his father 602 and one from his mother 604. In the example shown in FIG. 6, eight genetic markers 610 are analyzed representing a first haplogroup 612 and a second haplogroup 614. Preferably, the genetic markers 610 within each haplogroup are in linkage disequilibrium. The size 616 of each genetic marker 610 is determined for a first allele and the combination of sizes represents a specific haplotype 618 of the first allele. The specific haplotype 618 is then assigned a random number shown as "1" in FIG. 6. Thus, all individuals having the same haplotype 618 depicted would be assigned to group "1." In the second allele from the mother, the haplotype 618' is determined by the combination of the sizes of each of genetic marker 610 on the second allele. In the depicted embodiment, the illustrated haplotype is assigned the number "2." This process is repeated for the second haplogroup 614, wherein 5 genetic markers 610 are analyzed and assigned the number "3" for a first allele and "5" for a second allele.

In the illustrated example, an individual assigned a "2" or "5" for a particular allele would be expected to be related to the individual represented in FIG. 6 through the maternal side of the family. As a way of further condensing the genetic identifier, individuals having the combination of "1" and "3" may be assigned to a group represented by number "6." A second group number (shown as "8") may be assigned to individuals having the combination of "2" and "5." Thus, the partial genetic identifier for this individual would be "68." As will be understood, the process of analyzing the set of genetic markers on a chromosome is repeated until all of the examined sets are categorized. For example, a third set of genetic markers may result in additional numbers being added to the genetic identifier. Thus, each number within the genetic identifier may correspond to a particular haplotype.

In step 140, the individual's genetic data 30' and genealogical data 40' are stored in the database 25 in association with the individual's genetic identifier. In a preferred embodiment, the genealogical data 40' include the given name and surname, date of birth and place of birth of at least three, preferably four, generations of successively lineal ancestors. Genealogical data 40' can also include information regarding the family medical history or any other known information regarding an ancestor. The genealogical data 40' can be stored in a family tree format wherein the tree and each placeholder on the tree is designated by a unique genetic identifier (FIG. 3). Deceased ancestors are assigned a unique genetic identifier based on a probability statement of the likelihood of the ancestor having a specific haplotype. Analytical programming 50 can retrieve and associate the genetic data 30 and genealogical data 40 corresponding to a particular unique genetic identifier or for a plurality of members of a population.

In step 200, the individual's genealogical records 40' are compared with the genealogical records 40 in the database 25. The comparison could consist, for example, of searching for similar given names and surnames. Analysis of strictly genealogical information may allow the inference of a biological relationship (step 230). Similarly, in step 210, comparison of the individual's genetic data 30' with the genetic data 30 of the database 25 could lead to the identification of a biological relationship (step 240). Preferably, the process progresses to step 220 wherein the individual's genetic data 30' is associated with the individual's genealogical data 40' and then compared with the genetic data 30 and genealogical data 40 in the database 25 by analytical programming 50. In step 300, a biological relationship can be inferred based on the results of the analytical programming 50. In step 310, the individual's genealogical data 40' can be amended to reflect the new biological relationship and stored in the database 25.

The present invention allows identification of biological relationships from two perspectives. First, "gene genealogy" traces descendants from a "founder" individual in the past to the present. Accordingly, the database 25 can be used to identify all descendants from a particular person based on genetic data 30 and genealogical data 40 by following an individual gene or genetic marker from the founder to the present. Thus, the present invention will preserve the genetic heritage of an individual and family for future generations with multiple implications for genealogical and medical progress in the future. Second, an "ascendancy chart" is measured from a living individual to the past and indicates possible contributors of genes to an individual. In this approach, the database 25 can be used to identify possible ancestors by examining genetic data 30 and genealogical data 40.

The database 25 of the present invention is continually expanding. For example, when a genetic sample is introduced into the database 25, it is provided a unique genetic identifier, cross-referenced with the existing genetic data 30 and stored in the database 25. If the genetic sample has corresponding genealogical data 40, genealogical data 40 is also added to the database 25. Both the genetic data 30 and genealogical data 40 are updated and amended after new biological relationships are identified. Theoretically, a database 25 having genetic samples from 100,000 individuals, representing 500 populations worldwide, and the corresponding genealogical records 40 of four successively lineal ancestral generations would be statistically large enough to include or exclude an unknown individual from any of these "populations." Populations can be defined in many ways, including, but not limited to, geographically, linguistically or culturally. The correlation of genealogical data provides a time dimension to a population by including the date of birth of ancestors and allows statistical assignment of genetic markers in a living individual to a location and a date in the past. This unique definition of "population" is used herein.

The present invention can be used to identify previously unknown biological relationships or to confirm, verify or resolve discrepancies in family trees. For example, one embodiment of the invention includes a method of correcting a genealogical family tree. Genetic data for a plurality of individuals is identified. This could include retrieving genetic data 30 from a database 25. A genealogical family tree having a plurality of placeholders is identified which might include retrieving genealogical data 40 from a database 25. The genetic data for each placeholder are identified and compared and each placeholder is placed in a unique location within the tree based on their genetic data. Any genetic discrepancies among the placeholders are noted. For example, the genetic data for one or more placeholders may be outside a genetic range such that it is statistically questionable whether a particular placeholder is genetically related to the rest of the placeholders in the family tree. Any placeholder whose genetic data are outside of a genetic range is designated as anomalous. The genetic data of the plurality of individuals are compared with the genetic data for each placeholder. This could include comparing the genealogical records 40 of the database 25 with the genetic data for each placeholder. In this process, individuals may be identified as having genetic data within the genetic range of the family tree. Therefore, it may be inferred that such individuals are potential placeholders within the family tree. The anomalous placeholder must then be resolved. For example, it may be determined that the anomalous placeholder was improperly included in a family tree, in which case, the anomalous placeholder is removed. In other cases, the placeholder may be moved to another location within the family tree. Alternatively, the potential placeholder may be positioned within the family tree.

The present invention can also be used to determine an individual's populational origin or to trace the migration of people through history. The present invention permits determination of the genetic composition of major populations throughout the world and could be used to establish genotypic links in each population and between each population. Further, when genealogical data are associated with genetic data, it will be possible to examine how quickly genes change and what factors influence change between generations. Individual families will be linked to their ancestral homelands and the contemporary populations that share a common genetic heritage.

The invention could be used to verify family stories, such as that the family is a descendant of George Washington, Abraham Lincoln or another famous person. The invention could also be used to link family trees. For example, two people may be identified as having statistically similar genetic markers. However, it may be determined that it is statistically likely that they only share a common ancestor within a certain number of generations. Based on the variations of their genetic markers, a unique genetic identifier can be created for a "linker" ancestor that estimates the linker ancestor's genotype. Thus, the present invention permits the production of unique identifications for peoples that do not have traditional name-based genealogies. This would allow the reconstruction of DNA-based genealogies and extend an understanding of human relationships worldwide.

The present invention also provides a method of determining levels of biological relatedness. A plurality of family trees and members thereof are provided as, for example, in the genealogical data 40 of a database 25. Genetic markers are identified for the members of the family trees. In a preferred embodiment, the genetic markers are stored as genetic data 30 in the database 25 in association with a unique genetic identifier. Genetic markers that are representative of the members are identified. Preferably, the representative genetic markers are within a predetermined confidence interval. At least one unique genetic marker is identified for each family tree. A genetic sample is obtained, assigned a unique genetic identifier and compared with the at least one unique genetic marker. The level of biological relatedness of the genetic sample with at least one family tree can be inferred based on the degree of correlation of the genetic sample and unique genetic marker.

Levels of biological relatedness can be further inferred by statistically correlating the genetic marker(s) within a predetermined confidence interval, thereby creating at least one genetically defined group. The defined group can be supplemented with genealogical data and the level of biological relatedness of the defined group can be statistically correlated. The genetic sample can be statistically correlated with the defined group such that the genetic sample is identified as a member of at least one defined group.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A method of reconstructing the genotype of a previously unidentified common ancestor among humans, said method comprising:

obtaining genetic samples from a plurality of humans;

analyzing the genetic samples using the polymerase chain reaction to determine a first data set comprising genetic information characterizing genetic markers in linkage disequilibrium for each member of the plurality of humans, wherein the genetic information includes autosomal genetic information, wherein the genetic information comprises a unique genetic identifier for each member of the plurality of humans, and wherein at least one of the genetic markers is identical by descent among humans within three to ten successive lineal ancestral familial generations of each other;

providing a computer readable storage medium comprising a database and analytical programming for cross-referencing and comparing genetic information and genealogical information;

inputting the first data set into the database;

inputting a second data set into the database, the second data set comprising genealogical information from the plurality of members;

evaluating the genetic information for homology among the genetic markers; and associating the genetic information of the first data set with the genealogical information of the second data set;

using the analytical programming to cross-reference and compare the associated genetic information of the first data set and the genealogical information of the second data set; and reconstructing a genotype of a common ancestor between at least two members of the plurality of humans using at least the genetic information of the at least two members of the plurality of humans, in the absence of a genetic sample from the common ancestor, the common ancestor being previously unidentified within the genealogical information of at least one member of the at least two members of the plurality of members at the time the method is performed, the common ancestor being within three to ten successive lineal ancestral familial generations of each of the at least two members, each generation being defined by a meiotic event, wherein the level of biological relatedness of the at least two members of the plurality of members is undetermined at the time the method is performed.

2. The method according to claim 1, wherein evaluating the genetic information for homology comprises identifying a plurality of chromosomal fragments in the first data set that are substantially identical by descent, and associating and displaying the genetic information of the first data set with the genealogical information of the second data set comprises correlating the substantially identical chromosomal fragments with the genealogical information in the second data set.

3. The method according to claim 1, wherein the first data set is in genetic haplotype form.

4. The method according to claim 1, wherein associating the genetic information of the first data set with the genealogical information of the second data set comprises representing the degree of correlation between the first and second data sets statistically.

5. The method according to claim 1, wherein the genetic markers in linkage disequilibrium comprise single-nucleotide polymorphisms (SNPs).

6. The method according to claim 1, wherein the identity of the common ancestor is previously unknown to at least two members of the at least two members of the plurality of humans.

7. The method according to claim 1, wherein the at least two members of the plurality of humans have at least two separate lines of descent from the common ancestor.

8. The method according to claim 1, wherein each of the genetic markers in linkage disequilibrium is represented at a specific location on a chromosome.

9. The method according to claim 1, wherein the method further comprises:

producing a physical genealogical record display comprising either the genotype of the common ancestor, or the at least two members of the plurality of humans positioned in a family tree or pedigree chart.

10. The method according to claim 9, wherein the physical genealogical record display further comprises information about the physical characteristics or personal accomplishments of the common ancestor.

11. The method according to claim 1, the method further comprising identifying and displaying the common ancestor.

12. The method according to claim 1, wherein the first data set comprises genetic information characterizing genetic markers on each of the 22 autosomal chromosomes for each member of the plurality of humans.

13. The method according to claim 1, the method further comprising determining the position of the common ancestor in a family tree or pedigree chart of one of the members.

14. The method according to claim 1, wherein using the analytical programming to cross-reference and compare the associated genetic information of the first data set and the genealogical information of the second data set results in the identification within a predetermined confidence interval of a plurality of common ancestors.

15. The method according to claim 14, wherein the method comprises displaying the plurality of common ancestors.

* * * * *